United States Patent [19]

Roberts

[11] Patent Number: 6,083,512
[45] Date of Patent: *Jul. 4, 2000

[54] MULTICOMPONENT CLOSTRIDIAL VACCINES USING SAPONIN ADJUVANTS

[76] Inventor: David S. Roberts, 1020 Rockhurst Dr., Lincoln, Nev. 68510

[ * ] Notice: This patent issued on a continued prosecution application filed under 37 CFR 1.53(d), and is subject to the twenty year patent term provisions of 35 U.S.C. 154(a)(2).

[21] Appl. No.: 08/536,970

[22] Filed: Sep. 29, 1995

Related U.S. Application Data

[63] Continuation of application No. PCT/US94/03395, Mar. 29, 1994, which is a continuation of application No. 08/038,428, Mar. 29, 1993, abandoned.

[51] Int. Cl.$^7$ ..................................................... A61K 39/08
[52] U.S. Cl. ...................... 424/247.1; 536/4.1; 435/842; 514/25; 514/885
[58] Field of Search ...................... 424/247.1; 435/842; 514/885, 25; 536/4.1

[56] References Cited

U.S. PATENT DOCUMENTS

| | | | |
|---|---|---|---|
| 3,883,425 | 5/1975 | Dorn | 210/23 |
| 4,292,307 | 9/1981 | Zemlyakova | 424/92 |
| 4,981,684 | 1/1991 | MacKenzie et al. | 424/88 |
| 5,043,158 | 8/1991 | Sleytr et al. | 424/92 |
| 5,084,269 | 1/1992 | Kullenberg | 424/88 |
| 5,593,697 | 1/1997 | Barr et al. | 424/490 |
| 5,736,139 | 4/1998 | Kink et al. | 424/164.1 |

FOREIGN PATENT DOCUMENTS 0180564  7/1986  European Pat. Off. .

OTHER PUBLICATIONS

Thomson et al., 1976, *Develop. Biol. Standard*, 32:265–269.
Reynolds et al., 1990, *Veterinary Immunology and Immunopathology*, 25:167–175.
The Merck Veterinary Manual, 5th ed., 1979, pp. 396–409, Merck & Co., Rahway, NJ.
Thomson et al., 1969, "Immunogenicity of a multicomponent clostridial oil emulsion vaccine in sheep", *Vet. Rec.*, 85:81–85 (1969).
Thomson et al., 1953, *Vet. Rec.*, 65:(42):659–663.
Sterne et al., 1962, "Immunisation of sheep with multi–component clostridial vaccines", *Vet. Rec.*, 74(34):909–913.
Kerry et al., 1979, *Vet. Rec.*, 105:551–554.
Lozano, E. A., 1981, *Am. J. Vet. Res.*, 42(9):1641–1644.
Webster et al., 1985, *Australian Vet. J.*, 62(4):112–114.
Farrag et al., 1987, *Assiut Vet. Med. J.*, 18(36):73–83.
Awad et al., 1986, *Assiut Vet. Med. J.*, 17(34):202–214.
Dalsgaard, K., 1974, "Saponin adjuvants", *Archiv. gesamte virusforschung* 44:243–254.
Baharsefat et al (1976), Arch. Inst. Razis vol. 28, pp. 51–56.
Seifert et al, Deutsche Tierarztliche Wochenschrift, vol. 90, (7), pp. 274–279, 1983.
Alpha–7 product insert, Anchor™, Boehringer Ingelheim Animal Health Inc., 1992.
Green et al., The Veterinary Record, May 2, 1987 pp. 435–439.
Haas, H F, Develop. Biol. Standard., vol. 32, pp. 167–172, 1976.
Marciani et al Vaccine 9:89–96, 1991.
Kensil et al J. Immunol 146(2):431–437, 1991.

*Primary Examiner*—James C. Housel
*Assistant Examiner*—Ginny Allen Portner
*Attorney, Agent, or Firm*—Peter C. Richardson; Paul G. Ginsburg; Alan L. Koller

[57] ABSTRACT

Novel multicomponent clostridial vaccine formulations using readily dispersible, non-depot adjuvants, such as saponin, are disclosed. The vaccines can be administered to cattle intramusculary or subcutaneously without the severe persistent local reactions, such as granulomas, abscesses, and scarring, normally seen with other multicomponent clostridial vaccines.

21 Claims, No Drawings

MULTICOMPONENT CLOSTRIDIAL VACCINES USING SAPONIN ADJUVANTS

This is a continuation of application(s) International application PCT/US94/033395 filed on Mar. 29, 1994 and which designated the U.S. which is a continuation of U.S. Ser. No. 08/038,428 filed on Mar. 29, 1993 now abandoned.

TECHNICAL FIELD

The present invention relates generally to vaccine compositions and methods of using the same. More specifically, the invention pertains to multicomponent clostridial vaccines made without stabilizing carriers or depot adjuvants, but rather with a readily dispersible, water-soluble adjuvant, saponin.

BACKGROUND OF THE INVENTION

The genus Clostridium is composed of anaerobic, spore-forming, rod-shaped bacteria. The organisms occur naturally in soil as well as in the intestinal tract of animals, including man. Pathogenic strains are acquired either by wound contamination or by ingestion. Members of the genus are responsible for a wide variety of diseases which, in the absence of vaccination, cause significant economic losses to the farming industry. Such diseases include red water disease, big head, blackleg, the enterotoxemias, infectious necrotic hepatitis, malignant edema, botulism and tetanus, among others.

Antibiotic treatment of clostridial infections is rarely predictable and often ineffective. Accordingly, such infections are generally controlled prophylactically, using vaccine compositions containing one or more clostridial bacterins or toxoids. See, e.g., U.S. Pat. Nos. 4,292,307; 4,264,588; 3,579,633; Webster, A. C., and Frank, C. L. (1985) *Austral. Vet. J.* 62:112–114; Kerry, J. B., and Craig, G. R. (1979)*The Veterinary Record* 105:551–554; Sterne et al. (1962)*The Veterinary Record* 74:909–913. Clostridial toxoids are soluble proteins of relatively low antigenicity and, traditionally, poor stability. Thus, clostridial vaccines require adjuvants in order to increase antigenic potency and enhance stability. In particular, aluminum compounds, which are capable of adsorbing and/or precipitating clostridial toxoids, as well as retaining the toxoids at the injection site, are typically used. See, e.g., Thomson, R. O., and Knight, P. A. (1976) *Develop. Biol. Standard* 32:265–269; Thomson et al. (Jul. 26, 1969) *The Veterinary Record* pp. 81– 85. Other potent depot adjuvants, such as water-in-oil emulsions and carbopol, have also been used in clostridial vaccines. The above-described adjuvants, although increasing antigenicity, usually provoke severe persistent local reactions, such as granulomas, abscesses and scarring, when injected subcutaneously or intramuscularly. These local reactions are, in turn, responsible for carcass blemish which requires expensive trimming, a consideration when the vaccine has been injected into muscle tissue destined to be a valuable cut of meat.

Saponins are glycosidic natural plant products, grouped together based on several common properties. The saponins are surfactants, a characteristic illustrated by their tendency to foam when shaken. Saponins are able to lyse red blood cells, form complexes with cholesterol and are toxic to fish. Saponins have been employed as adjuvants in a number of vaccine compositions including vaccines against protozoal infections (U.S. Pat. No. 4,767,622), canine distemper vaccines (U.S. Pat. No. 5,178,862), vaccines against foot and mouth disease, among others. Awad et al. (1986) *Assiut Vet. Med. J.* 17:201–214 describe a comparison of single component blackleg vaccines including either alum, aluminum gel with saponin or oil adjuvants. However, the use of soluble adjuvants that are readily dispersed from the injection site, and have no depot effect, such as saponin, with a multicomponent clostridial vaccine, has not heretofore been described.

DISCLOSURE OF THE INVENTION

The present invention is based on the surprising discovery that the water-soluble adjuvant, saponin, can be used in place of a depot adjuvant in multicomponent clostridial vaccines for cattle. The vaccines are safe and nontoxic.

Accordingly, in one embodiment, the invention is directed to a multicomponent clostridial vaccine composition comprising two or more clostridial immunogens and a dispersible, soluble adjuvant.

In another embodiment, the subject invention is directed to a multicomponent clostridial vaccine composition comprising:

(a) clostridial bacterins or toxoids derived from each of *Clostridium chauvoei, Clostridium septicum, Clostridium novyi, Clostridium sordellii, Clostridium perfringens*, Type C and *Clostridium perfringens*, Type D; and (b) a saponin adjuvant.

In yet another embodiment, the invention is directed to a multicomponent clostridial vaccine composition comprising:

(a) clostridial bacterins or toxoids derived from each of *Clostridium haemolyticum, Clostridium chauvoei, Clostridium septicum, Clostridium novyi, Clostridium sordellii, Clostridium perfringens*, Type C and *Clostridium perfringens*, Type D; and (b) a saponin adjuvant.

Still other embodiments of the present invention are directed to methods of preventing or treating clostridial infection in a bovine animal, and methods comprising administering effective amounts of the subject vaccine compositions to the bovine animal.

In particularly preferred embodiments, the administering is done intramuscularly or subcutaneously.

These and other embodiments of the subject invention will readily occur to those of ordinary skill in the art in view of the disclosure herein.

DETAILED DESCRIPTION

The practice of the present invention will employ, unless otherwise indicated, conventional techniques known in the art of clostridial microbiology and immunology. Such techniques are explained in, e.g., Sterne and Batty (1975) *Pathogenic Clostridia* (Butterworths, Boston); Joint OIE-1ABS "Symposium on Clostridial Products in Veterinary Medicine" in *Developments in Biological Standardization*, Vol. 32, S. Karger, Basel (1976).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

By "saponin" is meant any of the sapogenin glycosides found in a wide variety of plants, as well as derivatives thereof, which are capable of increasing the potency of an antigen administered therewith. The sapogenin moiety is generally a steroid, a triterpenoid or a steroidalcaloid. The sugar moiety may vary greatly and can be, e.g., a glucose, galactose, pentose, methylpentose, among others.

A "multicomponent" clostridial vaccine composition refers to a vaccine derived from cultures of two or more serotypes of the same clostridial species and/or cultures derived from different clostridial species. A multicomponent vaccine will generally be derived from 2 to 15 different serotypes or species, more usually 2 to 10 different serotypes or species, depending on the diseases in question and the subject being treated.

An "immunogen" refers to a substance that, when introduced into an animal, stimulates an immunological response, as defined below. For purposes of the present invention, an immunogen refers to a whole organism (live, killed or attenuated), a preparation separate and discrete from a whole organism with which the preparation is associated in nature (e.g., a toxoid preparation made by inactivating a toxin released from the organism or a protein contained in a cell free extract derived from the whole organism), or a molecule containing one or more epitopes that will stimulate an immunological response.

An "immunological response" to a composition or vaccine is the development in the host of a cellular and/or antibody immune response to the composition or vaccine of interest, such that clostridial disease symptoms are either prevented or reduced.

By "bovine subject" is meant any of the various cow or ox species, whether male or female. The term does not denote a particular age. Thus, both adult and newborn animals are intended to be covered.

B. General Methods

Central to the present invention is the surprising discovery that stable, potent, multicomponent clostridial vaccines can be made without the use of depot adjuvants. In particular, the present invention provides for vaccines including rapidly dispersed, soluble adjuvants, that is, adjuvants that are not retained at the injection site for a significant period of time, thereby exhibiting low tissue reactivity. The vaccines can be administered intramuscularly and subcutaneously without the harmful side effects and chronic inflammatory responses that produce granulomas and abscesses, seen with other clostridial vaccine compositions when administered via these routes.

The vaccines are polyvalent, that is, they are derived from cultures of two or more clostridial serotypes and/or from different species of Clostridium. Accordingly, the immunogens can be derived from any of the clostridial species and serotypes thereof, depending on the disease or diseases targeted, such as, but not limited to *C. perfringens; C. septicum; C. tetani; C. chauvoei; C. novyi; C. sordellii; C. haemolyticum; C. botulinum*; and serotypes of these species.

Of particular interest, are multicomponent vaccine compositions derived from bacterins of *C. chauvoei* and toxoids of *C. haemolyticum, C. chauvoei, C. septicum, C. novyi, C. sordellii* and *C. perfringens*, Types C and D. Such a multicomponent vaccine composition is termed an "8-way" vaccine herein because it provides immunity not only against the specific organisms identified, but also against *C. perfringens*, Type B. Another particularly preferred vaccine contains the same fractions as above, with the exception of *C. haemolyticum* and, hence, is referred to as a "7-way" vaccine.

Non-clostridial antigens may also be added to the vaccines to afford protection against a wide spectrum of diseases. For example, antigens derived from *Moraxella bovis, Haemoiphilus somnus, Pasteurelia hemolytica*, various respiratory viruses, as well as others, can be added to the multicomponent clostridial vaccine compositions of the present invention for use bovine subjects.

The clostridial immunogens are generally provided as toxoids (inactivated toxins) and/or as bacterins (killed, inactivated whole cultures) and can be prepared using conventional methods, well known in the art. For example, the organisms of interest are grown in a suitable medium under anaerobic conditions and controlled conditions of temperature, pH, and so forth, readily determined by a skilled artisan. Suitable media are generally aqueous solutions of peptones, usually at concentrations of 1 to 4% (w/v), which may be fortified with extracts of yeast or organs such as muscle, liver and pancreas, or with vitamins and other growth factors. A sugar, such as glucose, is added as a source of carbon and energy. Reducing agents, such as cysteine HCl, may also be added in low concentrations, e.g., 0.01 to 0.05% (w/v). Organisms are generally incubated for 4 to 72 hours, or longer, depending on the rate of growth or toxin production of the particular culture. The culture is then processed as follows.

Cultures are first inactivated using formalin (Formaldehyde Solution, USP) at an appropriate concentration, temperature and pH, for a period of 1 to 5 days, depending on the particular culture. It is preferred to minimize the exposure to formaldehyde. Inactivation kills the bacteria and converts the toxins to harmless, but effectively antigenic, toxoids. The procedures for inactivating bacterial cultures are well known to, or readily determined by, one of skill in the art.

If bacterins are desired, inactivated cultures may then be left whole or the killed bacteria separated from the medium by i.e., centrifugation and/or filtering. The cells may be further purified using conventional means, such as by additional centrifugation and/or dialysis.

If toxoids are to be used in the vaccine compositions, the inactivated cultures can be concentrated and toxoids partially purified by salting out from the filtrate, using i.e., ammonium sulphate, or by molecular filtration, with or without diafiltration. The toxoids can be further purified by dialysis or centrifugation to eliminate salts. Any residual inactivating agent can be partially or completely neutralized using a neutralizer such as a sodium bisulfite solution, added to between about 0.1 to 0.25% v/v. See, e.g., U.S. Pat. Nos. 3,579,633; 4,264,588; and 4,292,307; as well as Lozano, E. A. (1981) *Am. J. Vet. Res.* 42:1641–1644, for procedures for producing clostridial toxoids, all incorporated herein by reference in their entirety.

The above-described bacterins and toxoids are administered in vaccine compositions including a readily dispersible (i.e., non-depot), soluble adjuvant, thereby avoiding chronic irritation at the injection site. Such adjuvants include, for example, mild oil-in-water emulsions made with mineral oil, such as, for example, Amphigen (U.S. Pat. No. 5,084,269) and cytokines, such as any of the various interleukins or interferons.

Particularly preferred dispersible, non-depot adjuvants for use with the present vaccine compositions are saponins. Saponins can be obtained commercially, from, e.g., Berghausen Corporation, (Cincinatti, Ohio); Sigma Chemical Co. (St. Louis, Mo.), Aldrich (Milwaukee, Wis.), Alfa (Ward Hill, Mass). Alternatively, saponins can be extracted from any of many plant species, such as from Gypsophilia sp., Saponaria sp., *Quillaja saponaria, Quillaja molina*, the galenicals such as *Akebia quinata, Fatsia japonica, Caulophyllum robustum, Hedera rhombea, Clematis chinensis, Pulsatilla cernua, Sapindus mukurossi, Panax japonicum, Glycyrrhiza glabra, Glycyrrhiza uralensis, Polygala senega, Platycodon grandiflorum, Polygala tenuifolia, Achyranthes fauriei, Achyranthes bidentata, Cyclamen europaeum, Primula officinalis, Bupleurum falcatum, Panax ginseng,*

*Panax notoginseng, Panax quinquefolium*, among others. Methods for extracting saponins from these sources are known in the art. See, e.g., U.S. Pat. Nos. 5,057,540 and 4,501,734, as well as International Publication No. WO88/09336, incorporated herein by reference in their entirety.

The vaccine compositions are generally formulated with a pharmaceutically acceptable vehicle or excipient. Suitable vehicles are, for example, water, saline, dextrose, glycerol, ethanol, or the like, and combinations thereof. In addition, if desired, the vehicle may contain minor amounts of auxiliary substances such as wetting or emulsifying agents and pH buffering agents. Although the inactivating agents used to produce the toxoids also serve as preservatives, additional preservatives can also be added to the vaccine formulations. Such preservatives are known in the art and include thimerosal, phenol and phenolic compounds, as well as antibiotics. Suitable vaccine vehicles and additives are known, or will be apparent, to those skilled in the art. See, e.g., *Remington's Pharmaceutical Sciences*, Mack Publishing Company, Easton, Pa., 18th edition, 1990. Particularly preferred compositions are composed of an aqueous suspension or solution containing the clostridial components, preferably buffered at a pH of approximately 7.

For example, injectable vaccine formulations are prepared by combining an effective amount of two or more of the bacterins and/or toxoids prepared as described above, in proportions determined by their assayed antigenic content, the exact amount being readily determined by one skilled in the art. For purposes of the present invention, an "effective amount" of a clostridial component will be that amount required to generate an amount of circulating antibody sufficient to prevent or reduce clostridial disease symptoms. Such amounts can be expressed using any of several units. For example, effective amounts of clostridial bacterins are usually expressed in terms of opacity or absorbency units (O.U. or A.U., respectively). These units are based on the optical density (O.D.) of the culture, as measured at a suitable wavelength, such as 625 nm. The O.D. value is then multiplied by the volume of the culture in one dose of vaccine. For example, an antigen dose of three O.U. would be provided by 0.5 ml of culture having an O.D. of six. Effective amounts of toxoids may be measured in terms of L+. An L+ unit of toxoid is equivalent to one unit of standard antitoxin, as determined by toxin-antitoxin titration in mice. (B. C. Jansen in *Developments in Biological Standardization*, Vol. 32, P. 91, S. Karger, Basel (1976). Effective amounts may also be measured in mice based on the minimum lethal dose (MLD), the dose that is lethal to at least 80% of the mice tested. Effective amounts can also be expressed with respect to total combining power (TCP) units, determined using immunosorbant assays to measure the ability of the toxoid in a culture to blanket and neutralize the combining sites on an antitoxin molecule of a standardized antiserum.

Effective amounts of typical clostridial components are as follows:

*C. chauvoei*—about 1.5–4 O.U., preferably about 2–2.5 O.U., and optimally about 2.28 O.U.;

*C. septicum*—about 500–2000 MLD, preferably about 800–1200 MLD, and optimally about 900 MLD before inactivation;

*C. novyi*—about 5000–30000 MLD, preferably about 10000–20000 MLD, and optimally about 15,000 MLD before inactivation;

*C. sordellii*—about 25–100 L+, preferably about 40–60 L+, and optimally about 50 L+ before inactivation;

*C. perfringens*, Type C—about 200–500 L+, preferably about 300–400 L+, and optimally about 375 L+ before inactivation;

*C. perfringens*, Type D—about 50–200 L+, preferably about 80–120 L+, and optimally about 100 L+ before inactivation; and optionally

*C. haemolyticum*—about 150–500 L+, preferably about 250–300 L+, and optimally about 270 L+ before inactivation. Whole *C. haemolyticum* cells can also be added in an amount of about 2–8 O.U., more preferably about 4–5 O.U., and optimally about 4.5 O.U. Additional effective amounts of these and other clostridial antigens will be readily determined by those of skill in the art using standard dose response curves.

The dispersible, non-depot adjuvant is generally added to a final concentration of between about 0.01% w/v to about 0.1% w/v, more preferably about 0.03% w/v to about 0.08% w/v and optimally to about 0.05% w/v. After assembly, sterile water or another suitable vehicle can be added to the required volume. The pH is then adjusted, generally to a value between pH 6.5 to 7.5. Residual formaldehyde content can be assayed in terms of formalin and adjusted, if necessary, to not more than 0.3% (v/v), and preferably, not more than 0.2% (v/v), in order to avoid the destabilizing effect of formaldehyde on unadsorbed clostridial toxoids during long-term storage. Most preferable, formalin content is kept to 0.2%, or less, during storage of the vaccine compositions.

To immunize a bovine subject, the vaccine compositions of the present invention are generally administered parenterally, preferably by intramuscular or subcutaneous injection. Other modes of administration, however, such as intraperitoneal and intravenous injection, are also acceptable. The quantity to be administered depends on the animal to be treated, the capacity of the animal's immune system to synthesize antibodies, the degree of protection desired and the particular clostridial infection being targeted. For example, to immunize cattle with the clostridial vaccine compositions described above, generally between 0.5 ml to 10 ml will be administered, more preferably 1 to 5 ml. Other effective dosages can be readily established by one of ordinary skill in the art through routine trials.

The subject is immunized by administration of the vaccine formulation, in at least one dose, and preferably two or more doses. However, the animal may be administered as many doses as is required to maintain a state of immunity against clostridial infection. For example, boosters given at regular intervals, i.e., at six months or yearly, may be desirable in order to sustain immunity at an effective level.

For optimal results, the above vaccine compositions may be administered to animals prior to weaning, with a second dose given at weaning age. Pregnant animals, that have not previously been vaccinated, can be administered two doses, one near the end of the gestation period. In animals previously vaccinated, a single booster can be administered prior to delivery.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of an 8-way Multicomponent Clostridial Vaccine Including a Saponin Adjuvant An 8-way clostridial vaccine was formulated using *C. chauvoei, C. septicum, C. novyi, C. sordelli, C. perfringens*

Type C and *C. perfringens* Type D, as follows. (The vaccine is termed an 8-way vaccine because it provides protection not only against the organisms listed, but also against *C. perfringens* Type B.)

The above clostridial species were cultured using techniques well known in the art. Cultures were monitored by measuring the optical density at 625 nm. When the optical density of the cultures reached a maximum, formalin was added to a final concentration of 0.7% (v/v) to 0.8% (v/v). Cultures were then inactivated for approximately 1 to 3 days.

After inactivation, the *C. perfringens* cultures were clarified aseptically by centrifugation and stored at 4° C. If necessary, the inactivated, clarified cultures were concentrated by ultrafiltration to reduce the culture volume required for serial assembly and to aid in standardization of the product.

In order to avoid destabilization effects that might be caused by higher formalin concentrations in the absence of aluminum hydroxide gels, sodium bisulfite solution (37% (w/v) was added to all cultures when processing was completed (i.e., after concentration and clarification), to neutralize residual free formalin in excess of 0.2%.

The cultures were combined so that each dose of vaccine contained a standard amount of each culture fraction as follows: *C. chauvoei*—2.28 O.U., *C. septicum*—900 MLD, *C. novyi*—15,000 MLD, *C. sordelli*—50 L+, *C. perfringens* Type C—375 L+, *C. perfringens* Type D—150 L+, *C. haemolyticum*—270 L+ and 4.5 O.U. bacterial cells.

The volume of each culture required was determined by dividing the amount of antigen required per dose by the antigen content of the culture used, and then multiplying by the number of doses required.

For example, the pre-inactivation toxin assay of a *C. novyi* culture showed it to contain 80,000 MLD/ml. the culture was standardized to 15,000 MLD/dose. The amount of culture required for a 1500 liter serial of 300,000 doses was: (15,000/80,000)×300,000=56.25 liters.

An exemplary serial assembly was performed as follows:

Assuming that finished culture components were available which had the following calculated antigen values:

| | | |
|---|---|---|
| i. | *C. chauvoei* | OD 12.0 |
| ii. | *C. septicum* | 3,000 MLD/ml |
| iii. | *C. novyi* | 80,000 MLD/ml |
| iv. | *C. sordelli* | 70 L+/ml |
| v. | *C. perfringens* Type C | 400 L+/ml |
| vi. | *C. perfringens* Type D | 120 L+/ml |
| vii. | *C. haemolyticum* | 360 L+/ml and OD 6.0 |

A serial of 1500 liters was assembled from the components as shown in Table 1.

TABLE 1

| Component | Volume (L) |
|---|---|
| *C. chauvoei* | 57 |
| *C. septicum* | 90 |
| *C. novyi* | 56.25 |
| *C. sordelli* | 214 |
| *C. perfringens* Type C | 281.25 |
| *C. perfringens* Type D | 375 |
| *C. haemolyticum* | 275 |
| Total culture volume | 1298.5 |
| | 7.5 L sterile saponin solution (10% w/v) |
| | 194 L sterile water |
| Total Volume | 1500 L |

The adjuvant, saponin, had a final concentration of 0.05% (w/v). the formalin concentration of the product was tested again and adjusted to 0.15–0.2%. The formalin was the only preservative. The pH of the assembled serial was adjusted to 6.8–7.0.

EXAMPLE 2

Potency of the Multicomponent Clostridial Vaccine

An 8-way vaccine prepared as described in Example 1 above was subjected to potency tests in rabbits and guinea pigs. USDA standard tests (9 CFR 113.106–.112) were used for each organism except *C. septicum*, for which no USDA test exists. In addition to the standard guinea-pig test, the *C. haemolyticum* antitoxin responses were titrated.

All the antitoxin titrations were done on the serum from a single batch of vaccinated rabbits. At least eight rabbits, weighing four to eight pounds, were injected subcutaneously with one-half of the cattle dose, twice at an interval of 20–23 days. The rabbits were bled 14 to 17 days after revaccination. Serum from at least seven rabbits was pooled and the different antitoxins assayed.

As Table 2 shows, the product met or exceeded all the potency standards. The *C. haemolyticum* component performed very well in both the official guinea-pig potency test and the unofficial antitoxin-response test in rabbits.

TABLE 2

Laboratory Animal Potency Tests on Clostridial 8-way Vaccine

| | Rabbit Antitoxin (Units/ml of serum) | | | | | | Guinea Pig | |
|---|---|---|---|---|---|---|---|---|
| Challenge | septicum | novyi | sordellii | perfringens C | perfringens D | haemolyticum | Alive/Total chauvoei | haemolyticum |
| Experimental Vaccine | 4 | 4 | 4 | 20 | 2 | 20 | 10/10* | 9/9* |

TABLE 2-continued

Laboratory Animal Potency Tests on Clostridial 8-way Vaccine

| Challenge | Rabbit Antitoxin (Units/ml of serum) | | | | | | Guinea Pig | |
| --- | --- | --- | --- | --- | --- | --- | --- | --- |
| | septicum | novyi | sordellii | perfring-ens C | perfring-ens D | haemoly-ticum | Alive/Total chauvoei | haemoly-ticum |
| USDA Potency Standards | 1** | 0.5 | 1 | 10 | 2 | 10 | 7/8 | 7/8 |

*all healthy
**in-house standards

EXAMPLE 3

Preparation of a 7-Way Multicomponent Clostridial Vaccine Including a Saponin Adjuvant A 7-way multicomponent clostridial vaccine was prepared as described in Example 1, except that the *C. haemolyticum* component was not included in the formulation. This vaccine was compared with an identical vaccine with no adjuvant, as well as with a commercially available multicomponent clostridial vaccine, Ultrabac 7 (SmithKline Beecham), which includes 25% Al(OH)$ left unvaccinated as negative controls. The vaccinates were injected with 5 ml, twice at a 4-week interval, and were bled at 2 weeks and again, 3 months later. Their antibody responses are shown in Tables 5 and 6. Guinea pigs were similarly vaccinated and the results shown in Table 7. As can be seen, the guinea-pig antibody responses support the cattle results. This study also showed that saponin was better than Al(OH)$_3$ gel (Ultrabac 7) in protecting guinea pigs against virulent challenge in the USDA standard potency test for *C. chauvoei*.

Thus, novel multicomponent clostridial vaccine compositions using saponin adjuvants, and methods for administering the same, are disclosed. Although preferred embodiments of the subject invention have been described in some detail, it is understood that obvious variations can be made without departing from the spirit and the scope of the invention as defined by the appended claims.

I claim:

1. A multicomponent clostridial vaccine composition, consisting of immunogens from two or more species or serotypes of Clostridium, a saponin adjuvant, and a pharmaceutically acceptable carrier.

2. A method of preventing or treating clostridial infection in a bovine animal, said method comprising administering an effective amount of the vaccine composition of claim 1 to said bovine animal.

3. The method of claim 2 wherein said administering is done via an intramuscular injection.

4. The method of claim 2 wherein said administering is done via a subcutaneous injection.

5. The vaccine composition of claim 1, comprising immunogens from six or more species or serotypes of Clostridium.

6. The vaccine composition of claim 1, wherein said species or serotypes are selected from the group consisting of *Clostridium perfringens, Clostridium septicum, Clostridium tetani, Clostridium chauvoei, Clostridium novyi, Clostridium sordellii, Clostridium haemolyticum* and *Clostridium botulinum*, and serotypes thereof.

7. A method of preventing or treating clostridial infection in a bovine animal, said method comprising administering an effective amount of the vaccine composition of claim 6 to said bovine animal.

TABLE 5

Responses of Cattle to 7-way Clostridial Vaccines
Antibody Titers of Serum Pools at 2 Weeks (8/group)

| | Agglutinin* | | | | Antitoxin iu/ml | |
|---|---|---|---|---|---|---|
| Adjuvant | chauvoei | septicum | novyi | sordellii | perfringens C | perfringens D |
| Saponin | 4096 | 8 | 4 | 20 | 40 | >8 |
| Al(OH)$_3$ gel (Ultrabac-7) | 512 | 8 | 1 | 20 | 40 | 4 |
| Unvaccinated Controls | 32 | <1 | <0.1 | <0.1 | <2.5 | <0.25 |
| USDA Potency Standards (Rabbits) | | 1** | 0.5 | 1 | 10 | 2 |

*C. chauvoei* makes no toxin and induces no antitoxin
**in-house standards

TABLE 6

Responses of Cattle to 7-way Clostridial Vaccines
Antibody Titers of Serum Pools at 3 Months (8/group)

| | Agglutinin* | | | | Antitoxin iu/ml | |
|---|---|---|---|---|---|---|
| Adjuvant | chauvoei | septicum | novyi | sordellii | perfringens C | perfringens D |
| Saponin | 1280 | 1 | 0.5 | 2 | <10 | 2 |
| Al(OH)$_3$ gel (Ultrabac-7) | 160 | 1 | 0.1 | <1 | <5 | 0.5 |
| Unvaccinated Controls | 40 | <1 | <0.1 | <0.1 | <2.5 | <0.25 |
| USDA Potency Standards (Rabbits) | | 1** | 0.5 | 1 | 10 | 2 |

*C. chauvoei* makes no toxin and induces no antitoxin
**in-house standards

TABLE 7

Responses of Guinea Pigs to Experimental 7-way Clostridial Vaccines or Ultrabac 7

| | Alive/Chall. | Antitoxin iu/ml | | | | |
|---|---|---|---|---|---|---|
| Adjuvant | chauvoei | septicum | novyi | sordellii | perfringens C | perfringens D |
| Saponin | 8/8, all healthy | 4 | 8 | 8 | 40 | 4 |
| Al(OH)$_3$ gel (Ultrabac-7) | 8/8, 2 sick | 2 | 8 | 8 | 40 | 2 |
| No Adjuvant | 4/8, 1 sick | <1 | <1 | <1 | <10 | 2 |
| Controls USDA Potency Standards | 7/8 or 12/16* | 1 | 0.5 | 1 | 10 | 2 |

*Guinea pig challenge, first and second stage

8. The method of claim 7 wherein said administering is done via an intramuscular injection.

9. The method of claim 7 wherein said administering is done via a subcutaneous injection.

10. The vaccine composition of claim 6, wherein the immunogens are clostridial bacterins or toxoids derived from each of *Clostridium chauvoei, Clostridium septicum, Clostridium novyi, Clostridium sordellii, Clostridium perfringens*, Type C, and *Clostridium perfringens*, Type D.

11. A method of preventing or treating clostridial infection in a bovine animal, said method comprising administering an effective amount of the vaccine composition of claim 10 to said bovine animal.

12. The method of claim 11 wherein said administering is done via an intramuscular injection.

13. The method of claim 11 wherein said administering is done via a subcutaneous injection.

14. The vaccine composition of claim 6, wherein the immunogens are clostridial bacterins or toxoids derived from each of *Clostridium haemolyticum, Clostridium chauvoei, Clostridium septicum, Clostridium novyi, Clostridium sordellii, Clostridium perfringens*, Type C, and *Clostridium perfringens*, Type D.

15. A method of preventing or treating clostridial infection in a bovine animal, said method comprising administering an effective amount of the vaccine composition of claim 14 to said bovine animal.

16. A multicomponent clostridial vaccine composition, consisting of immunogens from two or more species or serotypes of Clostridium, a saponin adjuvant, a pharmaceutically acceptable carrier, and a preservative.

17. The vaccine composition of claim 16, wherein the immunogens are clostridial bacterins or toxoids derived from each of *Clostridium chauvoei, Clostridium septicum, Clostridium novyi, Clostridium sordellii, Clostridium perfringens*, Type C, and *Clostridium perfringens*, Type D.

18. The vaccine composition of claim 16, wherein the immunogens are clostridial bacterins or toxoids derived from each of *Clostridium haemolyticum, Clostridium chauvoei, Clostridium septicum, Clostridium novyi, Clostridium sordellii, Clostridium perfringens*, Type C, and *Clostridium perfringens*, Type D.

19. A multicomponent clostridial vaccine composition, consisting of immunogens from two or more species or serotypes of Clostridium, and a saponin adjuvant.

20. A vaccine composition comprising: (i) immunogens from two or more species or serotypes of Clostridium; (ii) an antigen derived from one or more of *Moraxella bovis, Haemophilus somnus* or *Pasteurella haemolytica*; (iii) a saponin adjuvant; and (iv) a pharmaceutically acceptable carrier.

21. The vaccine composition of claim 20, further comprising a preservative.

\* \* \* \* \*

UNITED STATES PATENT AND TRADEMARK OFFICE
CERTIFICATE OF CORRECTION

PATENT NO. : 6,083,512
DATED : July 4, 2000
INVENTOR(S) : David S. Roberts and Don A. Dearwester It is certified that error appears in the above-indentified patent and that said Letters Patent is hereby corrected as shown below:

Title page: Item [75] under "Inventor", the patent should list Don A. Dearwester of Pfizer Inc., Groton, CT., as a co-inventor on the patent, in addition to David S. Roberts.

Item [73] should list Pfizer Inc. of 235 East 42$^{nd}$ Street, New York, N.Y. 10017, United States of America, as the assignee of the patent.

Signed and Sealed this

Third Day of April, 2001

*Attest:*

NICHOLAS P. GODICI

*Attesting Officer*     *Acting Director of the United States Patent and Trademark Office*